United States Patent
Timms

(10) Patent No.: US 8,137,692 B2
(45) Date of Patent: Mar. 20, 2012

(54) SOLID DEODORIZER FOR OSTOMY POUCHES

(76) Inventor: Cynthia G. Timms, Atlanta, GA (US)

( * ) Notice: Subject to any disclaimer, the term of this patent is extended or adjusted under 35 U.S.C. 154(b) by 441 days.

(21) Appl. No.: 12/552,834

(22) Filed: Sep. 2, 2009

(65) Prior Publication Data
US 2010/0055155 A1    Mar. 4, 2010

Related U.S. Application Data

(60) Provisional application No. 61/094,101, filed on Sep. 4, 2008, provisional application No. 61/184,430, filed on Jun. 5, 2009.

(51) Int. Cl.
    *A61K 9/70*      (2006.01)
    *A61L 9/014*     (2006.01)
    *A61K 8/02*      (2006.01)
    *A61Q 9/00*      (2006.01)

(52) U.S. Cl. .................. 424/443; 424/76.6; 424/400
(58) Field of Classification Search .............. None
See application file for complete search history.

(56) References Cited

U.S. PATENT DOCUMENTS

| | | | |
|---|---|---|---|
| 4,490,145 A | 12/1984 | Campbell | |
| 2003/0203009 A1 | 10/2003 | MacDonald | |
| 2003/0215417 A1* | 11/2003 | Uchiyama et al. | 424/76.2 |
| 2004/0062681 A1 | 4/2004 | Winston | |

FOREIGN PATENT DOCUMENTS
EP    0914862 A1    5/1999

OTHER PUBLICATIONS

International Search Report and Written Opinion for International Patent Application No. PCT/US2009/055761.

* cited by examiner

*Primary Examiner* — Ernst Arnold
*Assistant Examiner* — Christopher R Lea
(74) *Attorney, Agent, or Firm* — Charles L. Warner; Bryan Cave LLP

(57) ABSTRACT

A solid deodorizer (14) for use on the inside surface (12) of an ostomy pouch (10). The solid deodorizer include a deodorizing mixture (24) and a carrier (16) by which the deodorizer is attached to the inside of the pouch. The carrier has filaments (22) which are molded into the mixture, and an adhesive (20). The deodorizing mixture includes activated charcoal, glycerin, and wax, and may include one or more of sodium bicarbonate, stearic acid, and/or starch.

7 Claims, 1 Drawing Sheet

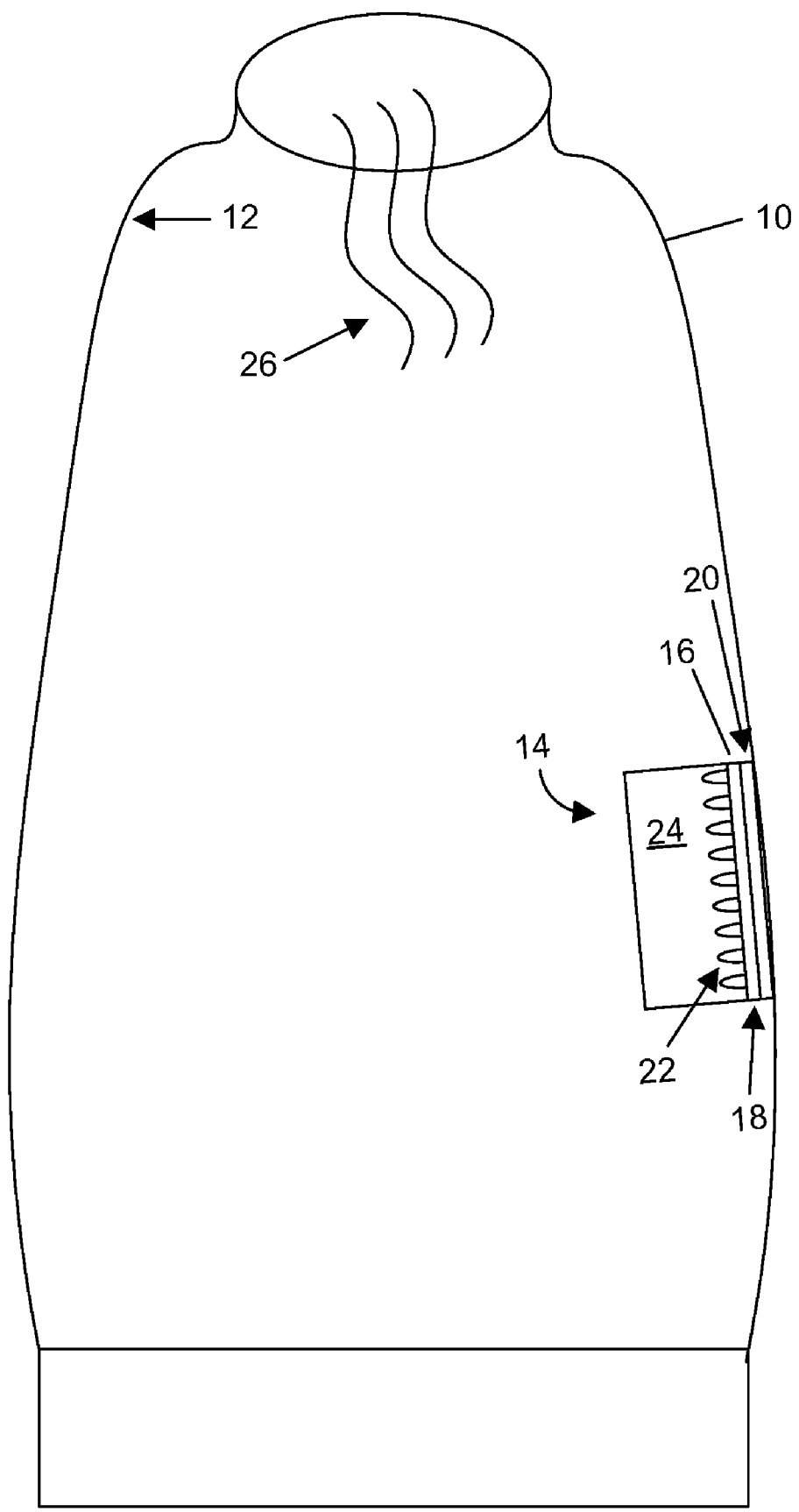

SOLID DEODORIZER FOR OSTOMY POUCHES

PRIORITY CLAIM

This patent application claims the priority of U.S. Provisional Patent Application Ser. No. 61/094,101, entitled "SOLID DEODORIZER FOR OSTOMY POUCHES", filed Sep. 4, 2008, and U.S. Provisional Patent Application Ser. No. 61/184,430, entitled "SOLID DEODORIZER FOR OSTOMY POUCHES", filed Jun. 5, 2009, the complete contents of both of which are hereby incorporated herein by reference.

BACKGROUND OF THE INVENTION

1. Field of the Invention

The present invention relates to solid deodorizers and, more particularly, to solid deodorizers for ostomy pouches.

2. Description of the Related Art

Due to heredity, injury, or disease, part or all of the large or small intestine of a person may have to be surgically removed, and the stoma (the remaining end of the large intestine or the small intestine) is brought up to the abdominal surface as an ostomy (a surgically created opening in the body for the discharge of bodily wastes). An ostomy pouch is then placed over the ostomy to collect the bodily wastes. A properly-fitted ostomy pouch neither leaks nor smells. An ostomy pouch is typically useful for several days before it must be replaced, but the pouch will eventually become full so one must periodically open the tail of the pouch (open end pouch), or detach the pouch from the ostomy (closed end pouch), and then empty the collected bodily wastes from the pouch.

During this emptying process the pouch is not covering the ostomy, or the tail of the pouch is open, so gases in the pouch may escape into the surrounding environment and create an undesirable odor. To avoid this problem a deodorizer is often placed in the ostomy pouch. One type of conventional deodorizer is a liquid, and another type of conventional deodorizer is a tablet. Unfortunately, in some prior art ostomy pouches, when the pouch is emptied the liquid or tablet is discarded along with the bodily wastes. Thus, the person is required to have on hand a replacement container of the deodorizing liquid or a replacement deodorizing tablet. Adding liquid to the pouch can be awkward and messy, and any spilled liquid deodorizer may stain or bleach clothing. A tablet does avoid the problem of spillage but, with respect to both conventional tablets and liquids, either some replacement liquid or a replacement tablet is required to be on-hand when the ostomy pouch is emptied. Replacement liquids and tablets are, however, easily forgotten, misplaced, or left behind due to size or weight considerations, especially when the person is traveling.

Prior art solutions to the problem of a non-odorous ostomy pouch include a variety of ways of delivering the deodorizing agent or removing the odor from the emanating gasses, such as liquids, tablets, powders, separate pouches, separate bags, separate sections for containing the deodorizer, capsules (rupturable or dissolvable), coatings on the inside of the pouch, filters (replaceable or not), and rupturable strips containing the deodorizer, the strips being bonded to, welded to, loose inside of, or adhesively affixed to, the pouch. The prior art also discloses various ingredients for the deodorizing agent, such as activated charcoal, glycerin, and hydrogen peroxide. Some of these solutions, however, pose problems in themselves if they must be directly handled. For example, a charcoal powder leaves a black residue which, if it gets on a person's fingers, can be easily transferred to the person's clothes; glycerin, if it gets on a person's fingers, can leave a greasy stain on the person's clothes; and hydrogen peroxide, if not carefully dispensed, can spill and cause bleach spots on a person's clothes.

Also, prior art liquid deodorizers are bulky and messy, prior art deodorizers which are loose in the ostomy pouch are prone to being lost when the pouch is emptied, deodorizers which are placed in the pouch at the time of manufacture may be prone to loss, breakage or leakage during shipment and storage, and special internal bags and compartments increase the cost of the pouch.

BRIEF SUMMARY OF THE INVENTION

A solid deodorizer is provided. In one embodiment, the solid deodorizer includes a deodorizing mixture and a carrier. Also, in one embodiment, the deodorizing mixture includes activated charcoal, wax, and glycerin. In another embodiment, in addition to the activated charcoal, wax and glycerin, the deodorizing mixture may include at least one of sodium bicarbonate, stearic acid, and/or starch. The carrier has a body with an adhesive on one surface of the body and a plurality of filaments projecting from another surface of the body, at least some of the filaments being at least partially embedded in the deodorizing mixture, and the adhesive being to attach the solid deodorizer to an object. One object to which the solid deodorizer may be attached is the inside of an ostomy pouch.

BRIEF DESCRIPTION OF THE DRAWING

The FIGURE illustrates an embodiment of the present invention in an exemplary environment.

DESCRIPTION OF THE INVENTION

The FIGURE illustrates an embodiment of the present invention in an exemplary environment. An ostomy bag 10 has an inside surface 12. Details of construction of ostomy bags are well known and are neither shown nor discussed here. The solid deodorizer 14 has a carrier 16 and a deodorizing mixture 24. The carrier 16 (which could also be called a fastener or some other name) has a body 18, an adhesive or an adhesive layer 20 on one surface of the body, and filaments 22 projecting from another surface of the body. The filaments 22 are shown as, and are preferably, but not necessarily, loops. The filaments 22 may also be hooks. At least some of the filaments 22 are at least partially embedded into the deodorizing mixture 24. Thus, the solid deodorizer is held to the inside of the ostomy pouch. As effluent 26 enters the ostomy pouch, some of the effluent washes over the solid deodorizer, thereby dissolving part of the solid deodorizer and releasing some of the components of the deodorizing mixture.

Although industrial production of the solid deodorizer is contemplated and expected, the inventor does not have access to industrial facilities. Therefore, with the limited facilities available to the inventor, one method of producing the solid deodorizer is discussed below.

The wax, glycerin soap base and stearic acid (if used) are melted in a double boiler over boiling water. The activated charcoal and sodium bicarbonate (if used) or starch (if used) are combined and mixed well, and then added to the melted wax, glycerin soap base and stearic acid mixture. The resulting mixture is stirred or mixed well, such as by blending with an electric blender or similar device, for approximately 15 to 20 seconds, or until a consistent (homogenous) blend is achieved. The mixture is then poured into 1⅛ inch×1⅛ inch×

1¼ inch molds (approximately 2.86 cm×2.86 cm×0.64 cm). Preferably, but not necessarily, while the mixture is still in liquid, or semi-liquid form, an additional amount (approximately 0.3 ml) of melted, high melt paraffin wax is injected into the center surface area of the mixture. The filaments of the adhesive-backed carrier are inserted into the mixture while the mixture is still in liquid or semi-liquid form. The injection of melted, high melt paraffin wax into the center surface area of the mixture strengthens the bond of the carrier to the mixture. The molds may be of any desired shape. In another embodiment the molds are 1¼ inch×1¼ inch×¼ inch (approximately 3.18 cm×3.18 cm×0.64 cm). In another embodiment the molds are circular molds having a diameter of 1⅛ inch and a thickness of ⅕ inch (approximately 2.86 cm and 0.51 cm, respectively).

While the resulting mixtures in the molds are still in a mostly liquid form, the carrier 16 is placed onto the mixtures so that the filaments 22 (such as the loops) protrude into the mixtures. Once the mixture has cooled, typically one to two hours later, the finished solid deodorizer is ready to use and can be removed from the molds. The cooling process may be accelerated by placing the filled molds inside a cooling device, such as, but not limited to, a refrigerator or freezer. This also facilitates the removal of the final product from the molds with minimal damage or breakage.

In one embodiment the carrier 16 is a circular ½ inch or ⅝ inch diameter (approximately 1.27 cm or 1.59 cm, respectively) adhesive carrier, which has entangling hooks, loops or fingers of material 22 which are thus embedded into the mixture while still in liquid or semi-liquid form and secure the mixture to the carrier. In another embodiment the carrier is ⅝ inch or ½ inch diameter (approximately 1.59 or 1.27 cm, respectively) Velcro™ sticky back general purpose hook and loop "coins" (currently marketed as Velcoin™ fasteners, also commonly referred to as dot or circle hook and loop fasteners). In another embodiment the carrier is a ¾ inch×½ inch (approximately 1.91 cm×1.27 cm) adhesive carrier. In still another embodiment, the carrier is an industrial strength Velcro™ strip with heavy duty adhesive backing. The carrier as purchased has a protective strip (not shown) which covers the adhesive prior to use. When the solid deodorizer 14 is to be applied, the user removes this protective strip, thereby exposing the adhesive 20, and then the user presses the solid deodorizer against the inside of the pouch, which presses the exposed adhesive against the inside of the pouch, thereby attaching the solid deodorizer to the inside of the pouch.

The paraffin wax is preferably, but not necessarily, commercially available High Melt-Point Straight Paraffin Wax MP163 by Peak Candle Supplies, Denver, Colo. Two 5 pound slabs of High Melt-Point Straight Paraffin Wax is commercially available from Peak Candle Supplies as item IGI-1260. In another embodiment the wax is Premium Candle Wax by Yaley Enterprises, Inc., Redding, Calif., sold in one-pound bags as item #110107.

The glycerin soap base may be, and is preferably, but not necessarily, commercially available "Essentials" clear glycerin soap brick by "Life of the Party"™, available at soapplace.com and candylandcrafts.com.

The activated charcoal is preferably, but not necessarily, USP1250CP (U.S. Pharmacopoeia) super fine grade activated charcoal powder, a premium USP food-grade charcoal made from coconut shells, acid-washed, and commercially available from several sources.

The sodium bicarbonate, if used, is food grade.

The stearic acid, if used, is food grade.

The starch is preferably, but not necessarily, pure corn starch, such as commercially available Argo™ 100% pure corn starch.

The components and sources are specified herein with particularity in order to comply with the "best mode" and "enablement" requirement of U.S. patent law. It will be appreciated that other sources of the components may be used. Further, although "food grade" components are specified in some cases, higher purity components, or lower purity components, may be required, or allowed, by the laws in a particular country. Therefore, the particular component specifications and sources therefore provided herein are not requirements for practicing the invention.

The solid deodorizer can be applied inside any clean ostomy pouch. It can also be used in a dirty ostomy pouch but the adhesive 20 may or may not stick properly, or at all, to the inside 12 of the ostomy pouch 10; the deodorizer, however, is still effective.

The deodorizing mixture will dissolve over 1 to 4 days depending on the consistency of the effluent and upon the particular formulation used. Thus, the carrier will be left inside of, and attached to, the pouch. The carrier is intended for one-time use and this provides for easy disposal of the pouch as the carrier need not be removed from the pouch. Also, in the event that a second solid deodorizer is desired or necessary, the carrier of the first solid deodorizer can be left in place and does not need to be removed.

Although use of the solid deodorizer with respect to an ostomy pouch has been described with particularity, the solid deodorizer may also be used to reduce or mask the smell of other types of pouches, systems, and containers (collectively, for convenience of reference, "collection pouches"), such as, but not limited to, urostomy pouches, fistula pouches, high output fecal pouches, bowel management bedside drainage systems, wound management bedside drainage systems (wound managers), and wall suction canisters in healthcare facilities. The solid deodorizer is also not limited to the sizes described herein and may be made larger or smaller for a particular application. For example, the solid deodorizer may be made smaller for disposable closed end fecal pouches, or it can be made larger for high output fecal pouches, fistula pouches, bowel management bedside drainage systems, and wound managers.

The solid deodorizer described herein thus has the advantages that it will not be accidentally lost when the pouch is emptied, it requires no special pouch design, it can be shipped and sold separately from the pouch, it is not messy to use, and it can be used with any pouch to which an adhesive or an adhesive strip can stick. It is also non-toxic, odorless, small, discrete, lubricating, easy to carry, and easy to use.

As mentioned, one use of the long lasting solid deodorizer is in an ostomy pouch. The solid deodorizer 14 has a deodorizing mixture 24 which is affixed to a carrier 16. The carrier 16 has an adhesive backing 20 that sticks to the inside of a clean ostomy pouch. Thus, the solid deodorizer will not be accidentally discarded when the pouch is emptied. In one formulation embodiment, the deodorizing mixture dissolves over a period of one to two days, depending on the consistency of the effluent. In another formulation embodiment, the deodorizing mixture dissolves over a period of two to four days. This provides freedom for the person for one to several days, at which time a new solid deodorizer can be attached inside an existing ostomy pouch or a new, clean ostomy pouch. The new ostomy pouch can then be applied. Thus, the need to carry a replacement liquid or tablet is avoided as this solid deodorizer will stay attached to the pouch even when the pouch is emptied.

Although the solid deodorizer can be carried separately from the ostomy pouch, it can also be placed in (and adhered to) the ostomy pouch in advance. Thus, if the person is traveling the person will not have to insert a solid deodorizer in the ostomy pouch at the time when the new ostomy pouch is being installed. This provides for additional convenience in that new ostomy pouches may be carried which are ready to use. Further, as the solid deodorizer is adhesively fixed to the inside of the pouch, it is not subject to being inadvertently dropped out of the pouch. In addition, the deodorizing mixture 24 is not hard like a tablet, or rupturable like a capsule, it is therefore much more tolerant of being bent, deformed, or compressed. Thus, the deodorizing mixture is less likely to be damaged during normal handling, and even while traveling in a purse, briefcase, or suitcase, whether as a separate item or whether it is inside of an ostomy pouch.

In one embodiment the deodorizing mixture comprises glycerin, wax, and activated charcoal. In another embodiment the deodorizing mixture comprises glycerin, wax, sodium bicarbonate (baking soda), activated charcoal and stearic acid. The glycerin may be provided as a glycerin soap base, which often contains other ingredients as well. One example of a glycerin soap base is provided herein. Preferably, but not necessarily, paraffin wax is used, but waxes other than paraffin wax may be used. Non-paraffin waxes, however, typically have lower melting points than paraffin wax and may require the use of a greater amount of stearic acid to achieve the desired dissolution rate. In still another embodiment, a starch may be added to the mixture to improve the performance. The use of starch, which is optional, slows down the rate at which the effluent dissolves the deodorizing mixture and thus also serves to control the dissolution of the deodorizing mixture.

The activated charcoal, sodium bicarbonate (if used), stearic acid (if used) and the glycerin soap base provide a deodorizing capability.

The glycerin soap base and stearic acid also lubricates the inside of the ostomy pouch, thus leaving the pouch cleaner when the effluent is emptied from the pouch.

The stearic acid both lubricates the inside of the ostomy pouch and facilitates a more consistent (homogenous) blend of the components of the mixture.

The wax and the stearic acid (if used) hold the activated charcoal, sodium bicarbonate (if used), and glycerin soap base. As the effluent dissolves and carries away some of the activated charcoal, sodium bicarbonate (if used) and glycerin soap base, the effluent also dissolves and carries away some of the wax and stearic acid (if used), thereby exposing more activated charcoal, sodium bicarbonate (if used), and glycerin soap base. Thus, fresh, replacement activated charcoal, sodium bicarbonate (if used) and glycerin soap base are constantly being provided. In this manner, the wax and stearic acid (if used) slow down the rate at which the deodorizing mixture is dissolved so that the solid deodorizer lasts for one to several days.

If excessive amounts of wax and/or stearic acid are used then the activated charcoal, sodium bicarbonate (if used) and the glycerin soap base may not be exposed at a rate which is adequate to control odors. Conversely, if too little wax and/or stearic acid (if used) are used, or if a low or medium melt point wax is used, then the activated charcoal, sodium bicarbonate (if used) and the glycerin soap base may be quickly washed into and covered by the effluent, and thereby provide inadequate odor control.

Although the proportions indicated herein are preferred, they are not critical, and different proportions may be used depending upon the desired results. For example, using more wax and/or stearic acid, or the use of a high melting point wax as opposed to low or medium melting point wax, decreases the rate of dissolution, but also decreases the deodorizing capability, in which case a larger solid deodorizer may be used, or two or more solid deodorizers may be used. As another example, using more glycerin soap base may serve to keep the inside of the ostomy pouch cleaner, but may decrease the usable lifetime of the solid deodorizer or make the deodorizing mixture turn into a liquid or liquid-like substance at some of the temperatures expected to be encountered in normal shipment, storage, and/or use.

Stearic acid is used to increase the melting point of the glycerin soap base and wax. The amount of stearic acid used is dependent, in part, on the glycerin soap base used, which may or may not contain stearic acid as well, and the type and melting point of the wax used. Paraffin wax typically can be purchased in low, medium and high melting point formulations. Non-paraffin waxes typically have lower melting points than paraffin wax, and so any formulation using non-paraffin wax may require the use of a greater amount of stearic acid to achieve the desired dissolution rate.

Generally, in one embodiment, there will be 104 to 122 grams glycerin soap base, 110 to 127 grams high-melting point paraffin wax, 2 to 10 grams stearic acid, 9 grams of activated charcoal, and 20 grams of sodium bicarbonate. Some specific formulations are provided below.

In one formulation, (dry weight of components) the deodorizing mixture comprises (dry weight of components):
  39%, or approximately 104 grams in solid form, (100 milliliters when melted) glycerin soap base;
  47% or approximately 127 grams in solid form (164 milliliters when melted) high-melt point paraffin wax;
  4% or approximately 10 grams in solid form (11 milliliters when melted) of stearic acid;
  3% or approximately 9 grams of activated charcoal; and
  7% or approximately 20 grams of sodium bicarbonate.

The above quantities will provide about 45 solid deodorizers, each being about 1⅛ inch×1⅛ inch×¼ inch (approximately 2.86 cm×2.86 cm×0.64 cm).

In another formulation, (dry weight of components) the deodorizing mixture comprises (dry weight of components):
  44%, or approximately 116 grams in solid form, (100 milliliters when melted) glycerin soap base;
  44% or approximately 116 grams in solid form (150 milliliters when melted) high-melt point paraffin wax;
  1% or approximately 3 grams in solid form (approximately 3.2 milliliters when melted) of stearic acid;
  3% or approximately 9 grams of activated charcoal; and
  8% or approximately 20 grams of sodium bicarbonate.

The above quantities will provide about 45 solid deodorizers, each being about 1⅛ inch×1⅛ inch×¼ inch (approximately 2.86 cm×2.86 cm×0.64 cm).

In another formulation, (dry weight of components) the deodorizing mixture comprises (dry weight of components):
  42%, or approximately 122 grams in solid form, (105 milliliters when melted) glycerin soap base;
  46% or approximately 110 grams in solid form (142 milliliters when melted) high-melt point paraffin wax;
  1% or approximately 2 grams in solid form (approximately 2.1 milliliters when melted) of stearic acid;
  3% or approximately 9 grams of activated charcoal; and
  8% or approximately 20 grams of sodium bicarbonate.

The above quantities will provide about 45 solid deodorizers, each being about 1⅛ inch×1⅛ inch×¼ inch (approximately 2.86 cm×2.86 cm×0.64 cm).

In another embodiment, the deodorizing mixture comprises (dry weight of components):
  2 parts (100 milliliters when melted) glycerin;

2 parts (150 milliliters when melted) wax;
1 heaping teaspoon (approximately 7 milliliters) charcoal; and
1 heaping teaspoon (approximately 7 milliliters) of starch.

The above quantities will provide about 45 solid deodorizers, each being about 1¼ inch by 1¼ inch by ¼ inch (approximately 3.18 cm×3.18 cm×0.64 cm).

In one embodiment, a softer solid deodorizer is made by using less wax and more stearic acid, which is useful for people with low output appliances, typically a colostomy pouch. In another embodiment, a harder solid deodorizer is made by using more wax and less stearic acid, which is useful for people with high output appliances, such as an ileostomy pouch.

The carrier 16 has filaments 22, fibers, or the like, which are embedded into the deodorizing mixture 24. The carrier 16 also has an adhesive strip 20 on back which can adhere to the inside 12 of the pouch 10. In one embodiment, the carrier 16 is an adhesive-backed Velcro™ strip or other similar adhesive-backed hook and loop type strip carriers. In another embodiment, the carrier is a Velcro Sticky Back Coin™ either ½ inch or ⅝ inch in diameter (1.27 cm, 1.59 cm, respectively), which is substantially the same product as the Velcro™ strip cut in a circular form. The Velcro hooks and/or loops are embedded into the deodorizing mixture 24 during formation of the mixture and firmly grip the deodorizing mixture. As previously mentioned, this bond is strengthened by injecting a small amount of melted, high melt paraffin wax into the center surface area of the mixture prior to embedding the carrier into the mixture. The adhesive backing 20 of the Velcro strip or coin then firmly binds the carrier 16, and therefore the deodorizing mixture 24, inside of and to the pouch 10. As a result, the undissolved deodorizing mixture is not discarded with the bodily wastes when the pouch is emptied. This design also allows the bodily wastes 26 to flow over and slowly dissolve the solid deodorizer 24 so that the contents will mix with the effluent to destroy the odor.

Although the preferred use of the solid deodorizer is with a carrier to affix the solid deodorizer to the inside of the ostomy pouch, some people are not comfortable with the idea of anything remaining in the pouch when it is emptied, so the solid deodorizer may also be used without the carrier.

Although the quantities of the various components have been specified, it will be appreciated, that variations of those relative quantities may be made to achieve certain desired benefits, and that small variations from the specified relative quantities may be made without substantially affecting the form or function of the deodorizer.

Various features and benefits of the present invention will become apparent upon reading the description of the various embodiments described herein, when taken in conjunction with the drawing and the claims.

Conditional language, such as, among others, "can", "could", "might", or "may", unless specifically stated otherwise, or otherwise understood within the context as used, is generally intended to convey that certain embodiments optionally could include, while some other embodiments do not include, certain features, elements and/or steps. Thus, such conditional language indicates, in general, that those features, elements and/or step are not required for every implementation or embodiment.

The invention claimed is:

1. A solid deodorizer, comprising:
   a deodorizing mixture including activated charcoal, wax, and glycerin; and
   a carrier having a body with an adhesive on one surface of the body and a plurality of filaments projecting from another surface of the body, at least some of the filaments at least partially embedded in the deodorizing mixture, and the adhesive to attach the solid deodorizer to an object.

2. The solid deodorizer of claim 1 wherein the deodorizing mixture further comprises at least one of sodium bicarbonate, stearic acid, or starch.

3. The solid deodorizer of claim 1 wherein the glycerin is embodied as a glycerin soap base.

4. The solid deodorizer of claim 1 wherein the wax is a paraffin wax.

5. The solid deodorizer of claim 1 wherein the deodorizing mixture further comprises stearic acid and sodium bicarbonate, and as:
   104 to 122 grams glycerin soap base;
   110 to 127 grams high-melting point paraffin wax;
   2 to 10 grams stearic acid;
   9 grams of activated charcoal; and
   20 grams of sodium bicarbonate.

6. The solid deodorizer of claim 1 wherein the deodorizing mixture further comprises starch, and as:
   100 milliliters glycerin soap base;
   150 milliliters high-melting point paraffin wax;
   7 milliliters of activated charcoal; and
   7 milliliters of starch.

7. The solid deodorizer of claim 1 wherein the filaments are shaped as at least one of loops or hooks.

* * * * *